United States Patent
Vignali et al.

(10) Patent No.: US 9,751,902 B2
(45) Date of Patent: Sep. 5, 2017

(54) ORGANIC TITANIUM DERIVATIVE AND PROCESS FOR THE PREPARATION THEREOF, INK CONTAINING THE DERIVATIVE AND CERAMIC DIGITAL PRINTING METHOD THAT USES THE INK

(71) Applicant: Graziano Vignali, Sasso Marconi (IT)

(72) Inventors: Graziano Vignali, Sasso Marconi (IT); Fabrizio Guizzardi, Bologna (IT)

(73) Assignee: Graziano Vignali, Sasso Marconi (IT)

( * ) Notice: Subject to any disclaimer, the term of this patent is extended or adjusted under 35 U.S.C. 154(b) by 0 days.

(21) Appl. No.: 15/123,874

(22) PCT Filed: Jul. 23, 2015

(86) PCT No.: PCT/EP2015/066868
§ 371 (c)(1),
(2) Date: Sep. 6, 2016

(87) PCT Pub. No.: WO2016/012538
PCT Pub. Date: Jan. 28, 2016

(65) Prior Publication Data
US 2017/0015687 A1    Jan. 19, 2017

(30) Foreign Application Priority Data
Jul. 24, 2014 (IT) .............................. MI2014A1350

(51) Int. Cl.
*C07F 7/28* (2006.01)
*B41J 2/01* (2006.01)
(Continued)

(52) U.S. Cl.
CPC .................. *C07F 7/28* (2013.01); *B41J 2/01* (2013.01); *C04B 41/82* (2013.01); *C08G 83/001* (2013.01);
(Continued)

(58) Field of Classification Search
CPC .. G03G 13/20; B01D 53/8609; C08G 63/183; C09D 1/00; B01J 21/063
See application file for complete search history.

(56) References Cited

U.S. PATENT DOCUMENTS 5,707,770 A * 1/1998 Tanikawa ............... G03G 13/20
    430/108.3
5,767,302 A * 6/1998 Ogi .......................... C07F 7/006
    257/E21.272

(Continued)

OTHER PUBLICATIONS

International Search Report for PCT Serial No. PCT/EP2015/066868 dated Oct. 22, 2015.

(Continued)

*Primary Examiner* — Stephen Meier
*Assistant Examiner* — John P Zimmermann
(74) *Attorney, Agent, or Firm* — McCormick, Paulding & Huber LLP

(57) ABSTRACT

Described is a production process for the preparation of an organic titanium derivative useful for the preparation of yellow inks for digital printing on ceramics, comprising the following steps:
(i) mixing an organic and/or inorganic compound of titanium (IV) and a 1,3-diol of formula:

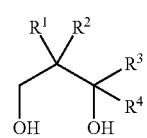

[1]

wherein $R^1$, $R^2$, $R^3$ and $R^4$ are independently selected from H and a linear or branched C1-C6 alkyl radical, (Continued)

in the presence of at least an organic solvent immiscible with water and subsequent removal of reaction by-products;

(ii) adding water to the reaction mixture in a $H_2O:Ti \geq 2$ molar ratio and subsequent removal of unreacted water and reaction by-products;

(iii) maturing the reaction mixture at a temperature of 180-200° C. for 16-50 hours.

Also described are the titanium derivative obtainable by means of the above-reported process, an ink that contains the derivative and a method of digital printing on ceramics that uses said ink.

12 Claims, 5 Drawing Sheets

(51) Int. Cl.

| | |
|---|---|
| C09D 11/033 | (2014.01) |
| C04B 41/82 | (2006.01) |
| C08G 83/00 | (2006.01) |
| C09D 11/02 | (2014.01) |
| C08K 5/00 | (2006.01) |
| C09D 11/322 | (2014.01) |
| C09D 11/38 | (2014.01) |
| C09D 11/40 | (2014.01) |

(52) U.S. Cl.
CPC ............ *C08K 5/0091* (2013.01); *C09D 11/02* (2013.01); *C09D 11/033* (2013.01); *C09D 11/322* (2013.01); *C09D 11/38* (2013.01); *C09D 11/40* (2013.01); *C04B 2235/3232* (2013.01)

(56) References Cited

U.S. PATENT DOCUMENTS

| | | | |
|---|---|---|---|
| 8,859,452 B2* | 10/2014 | Zhang | C07F 15/065 502/175 |
| 2005/0227008 A1* | 10/2005 | Okada | B01D 53/8609 427/372.2 |
| 2006/0008412 A1* | 1/2006 | Langlet | B01J 21/063 423/608 |
| 2007/0065649 A1* | 3/2007 | Matsui | C08G 63/183 428/220 |
| 2008/0090006 A1* | 4/2008 | Yoshinaka | C09D 1/00 427/212 |
| 2012/0035338 A1* | 2/2012 | Tan | C08F 10/00 526/123.1 |

OTHER PUBLICATIONS

Chemical Abstracts Service, Columbus, OH, 2009, Tsuboska, Masashi "Oil-based marking ink compositions giving water and solvent-resistant writings on nonabsorbing surfaces" XP002737516.

Chemical Abstracts Service, Columbus, OH, 2009, Kofuji, Michihisa et al "Titanium compound-container printing compositions, plastic sheet coated with ink compositions and laminated materials" XP002737517.

* cited by examiner

ORGANIC TITANIUM DERIVATIVE AND PROCESS FOR THE PREPARATION THEREOF, INK CONTAINING THE DERIVATIVE AND CERAMIC DIGITAL PRINTING METHOD THAT USES THE INK

CROSS REFERENCE TO RELATED APPLICATION

This application is entitled to the benefit of and incorporates by reference subject matter disclosed in International Patent Application No. PCT/EP2015/066868 filed on Jul. 23, 2015, and Italian Patent Application No. MI2014A001350 filed on Jul. 24, 2014, the contents of all of which are incorporated by reference herein.

FIELD OF THE INVENTION

The object of the present invention is an organic titanium derivative and a synthesis process of said derivative, a ceramic digital printing ink containing said organic titanium derivative and a ceramic digital printing method that makes use of said ink.

BACKGROUND OF THE INVENTION

In the ceramics field, digital printing decoration technology, generally through the use of ink-jet printers, has become established in the last decade. Digital printing has allowed a marked improvement in the aesthetic qualities of ceramic products, making it possible to produce decorations with extremely complex patterns, such as for example floor or wall tiles that reproduce the appearance of natural materials. The inks used in digital printing devices generally consist of a solvent or a mixture of solvents and one or more finely ground pigments dispersed in the solvent. Although they allow surface decorations to be produced, these inks are unable to penetrate the ceramic material onto which they are applied as they contain suspended solids, therefore the decorated surface must be covered with a protective layer, generally a transparent glaze (known as "crystalline" in the field), to prevent discolouration of the decoration due to mechanical wear and attack by both chemical an mechanical atmospheric agents. This makes producing unglazed ceramic materials using this type of inks impossible. Inks containing, in addition to the solvent, also completely soluble organic compounds of chromophore metals, can be used to produce unglazed products coloured also within the ceramic mass. These chromophore metals give rise to development of the colouration during firing of the coloured manufactured articles. In digital printing processes the desired colour is normally obtained by the subtractive mixing of the colours of the inks comprising the print set. Each ink set will therefore only be able to produce a certain range of colours (known as gamut) that represents a more or less broad portion of the colorimetric space: the broader the gamut produceable with a given ink set, the more colour tones are obtainable with that set. To obtain a sufficiently broad gamut, an ink set generally comprises an ink that is able to develop the colour yellow after firing.

It is known in the field that colourant solutions containing soluble compounds of chromium in combination with soluble compounds of Sb, Zn, Zr and/or Mn can be used to obtain the colour yellow in a colouring method of ceramic supports to which titanium dioxide is added (EP 894081). Alternatively, colourant solutions containing soluble compounds of Sb and/or W and soluble compounds of Ti can be used, said solutions being able to develop after firing the colour yellow on ceramic materials not mixed with a titanium dioxide additive (EP 940379). The simultaneous presence of chromium, antimony and titanium in the coloured portion of the ceramic material is therefore an essential requirement for development of the colour yellow after firing. The hue and saturation of the yellow obtained will largely depend on the quantity ratio of these chromophore metals in the coloured portion of the ceramic slurry.

Patent EP 1272574 describes a CMY ink set for digital printing on glazed ceramics based on organic solvents, wherein one of the inks useful for obtaining the colour yellow contains a mixture of soluble complexes of antimony and chromium and/or nickel, in combination with a source of titanium. According to one of the variants described in this patent, titanium is present in the ink in the form of a soluble compound, preferably titanium tetraisopropoxide (paragraph [0050]) or as a compound derived from another alkoxide (Example 4, paragraph [0075]). In the printing process, this ink can be indifferently applied to a conventional glaze or to a glaze mixed with an additive to which titanium dioxide has been added to intensify the development of the colour yellow.

Patent application WO 2009/077579 describes an alternative ink set for ceramic ink-jet printing wherein the yellow colour is obtained with an ink (composition C2) containing an organic compound of titanium in addition to a soluble organic compound of chromium or nickel in combination with a soluble organic compound of tungsten or antimony. In the case of an organic solvent-based ink, this organic compound of titanium is preferably titanium 2-ethylhexanoate. The described ink set is used in a digital printing method on ceramic materials mixed with titanium dioxide and amorphous silica as additives.

Although the inks for obtaining the colour yellow described in the previous patents can be used for ceramic digital printing, the titanium derivatives contained in these inks are extremely water sensitive and hydrolytically unstable compounds and easily give rise to precipitates on contact with water, which is generally present with a content of about 5% by weight in the unfired ceramic tiles; since these tiles have temperatures between the ambient temperature and 60-70° C. at the time of decoration, the water contained in the tiles evaporates during printing, ascends the conduits of the printing heads from which the inks are expelled and comes into contact with the inks themselves before these are printed, causing the precipitation thereof within the print devices. Consequently, use of the inks described in the previous patents leads to frequent clogging of the printing head nozzles and to a significant reduction in line production capacity due to the need to perform frequent maintenance, cleaning and replacement operations of the same printing heads.

Titanium derivatives poorly sensitive to water, such as those described in U.S. Pat. No. 2,643,262 and GB 1586671 have been known in the field for some time.

U.S. Pat. No. 2,643,262 describes organic titanium derivatives, called "glycol titanates", obtainable from the reaction of a titanium alkoxide and a 1,3-diol in titanium:diol molar ratios variable between 1:0.5 and 1:4. These titanium derivatives are generally complex monomers or polymers and can be used as adhesives, surfactants and additives. In Example 1, the patent illustrates the synthesis of a glycol titanate by reacting equimolar amounts of titanium tetraisopropoxide and 2-ethyl-1,3-hexanediol, in the presence of n-heptane as solvent.

GB patent 1586671 describes analogous titanium derivatives, to be used as transesterification catalysts, which can be obtained by reacting a titanium alkoxide and a 1,3-diol in Ti:diol molar ratios of between 1:1 and 1:2. In the description of the preparation of the catalyst J, titanium tetraisopropoxide and 2-ethyl-1,3-hexanediol are reacted in equimolar amounts in the presence of petroleum ether as the solvent. The titanium derivatives described in this patent are insensitive to moisture. However, when used in a mixture with organic compounds of chromium for the formulation of inks to obtain the colour yellow in ceramic digital printing, said titanium derivatives are not always compatible with the organic compounds of chromium and can also form hydrolytically unstable mixtures with these.

There is therefore a continuing need in the field need to provide organic titanium derivatives useful for the preparation of inks for digital printing on ceramics that are able to develop the colour yellow during firing of the decorated material and that are fully soluble in organic solvents, hydrolytically stable and compatible with organic compounds of chromium and/or nickel.

Object of the present invention is to provide an organic titanium derivative that has the above-cited characteristics as well as to provide a process for the preparation of said derivative, a ceramic digital printing ink containing said derivative and a digital printing method on ceramics that makes use of said ink.

SUMMARY OF THE INVENTION

These and other objects have been achieved with the present invention, which, in a first aspect thereof relates to a production process for the preparation of an organic titanium derivative having the required characteristics of solubility, hydrolytic stability and compatibility with organic chromium and/or nickel derivatives, said process comprising the following steps:
(i) mixing an organic and/or inorganic compound of titanium (IV) and a 1,3-diol of formula:

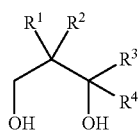

[1]

wherein $R^1$, $R^2$, $R^3$ and $R^4$ are independently selected from H and a linear or branched C1-C6 alkyl radical, in a Ti:diol molar ratio of between 1:0.85 and 1:1.20, preferably of between 1:0.95 and 1:1.05, in the presence of at least an organic solvent immiscible with water and subsequent removal of reaction by-products;
(ii) adding water to the reaction mixture in a $H_2O:Ti \geq 2$ molar ratio, preferably ≥3, more preferably between 5:1 and 3:1, and subsequent removal of unreacted water and reaction by-products;
(iii) maturing the reaction mixture at a temperature of 180-200° C. for 16-50 hours.

In a second aspect thereof, the invention relates to a titanium derivative obtainable by means of the above described process, consisting of a titanium-containing organo-inorganic polymer characterized in that the polymeric fraction having Log M≥3 has an at least bimodal molecular weight distribution and represents at least 70% by weight of the derivative.

The third aspect of the invention relates to an ink containing the above-described derivative, comprising:
(A) 6.0-12.0%, preferably 6.5-11.0% by weight, of Ti in the form of the titanium derivative of the invention;
(B) 0.5-2.0%, preferably 0.8-1.2% by weight, of Cr in the form of an organic compound of Cr(III) and/or 1.0-3.0% by weight of Ni in the form of an organic compound of Ni;
(C) at least an organic solvent selected from saturated or unsaturated, cyclic or acyclic, linear or branched, possibly halogenated aliphatic hydrocarbons, aromatic hydrocarbons, ethers, glycol ethers, esters, carbonates and mixtures thereof.

Lastly, in the fourth aspect thereof, the invention relates to a printing method that uses the above-described ink.

DETAILED DESCRIPTION OF THE INVENTION

Figure 1:
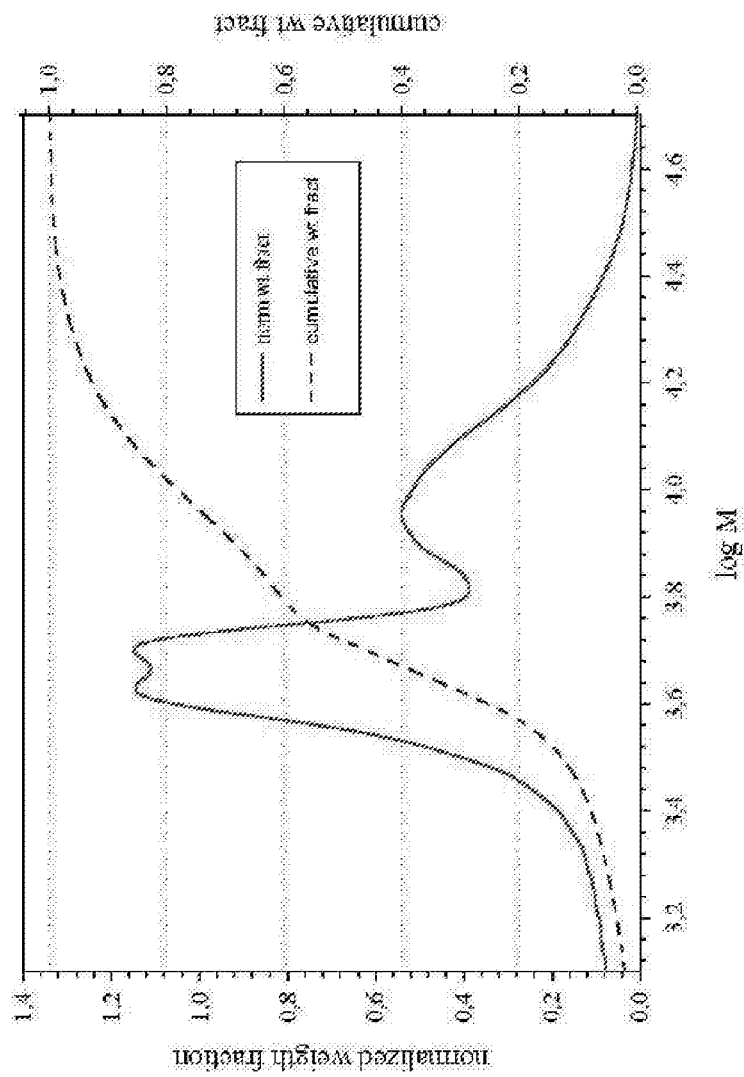
FIGS. 1, 2 and 4 report the distribution curves of the molecular weights of three different titanium derivatives of the invention.

In the description that follows, all percentage values that express the content of a component in a compound or composition, or the concentration of a component of a solution or an ink, are to be understood by weight unless specified otherwise.

The first aspect of the invention relates to a process for the production of the titanium derivative to be used in the production of inks.

Step (i) of the process of the invention provides for the mixing of an organic, inorganic or organo-inorganic compound of Ti(IV) with a 1,3-diol of the above-reported formula [1]. The inorganic compounds of Ti(IV) that can be used include titanium halides (e.g. titanium tetrachloride or titanium tetrabromide), titanium sulfate, titanium hydroxide, etc. The organo-inorganic compounds of Ti(IV) include for example chloro-isopropyl-titanate. The organic compounds of Ti(IV) that can be usefully employed include oxititanates such as for example titanium oxo-acetylacetonate or, preferably, titanium alkoxides of formula Ti(OR)$_4$, wherein R is linear or branched C1-C4 alkyl radical; examples of titanium alkoxides useful for the purposes of the invention are titanium tetramethoxide, titanium tetraethoxide, titanium tetra-n-propoxide, titanium tetra-n-butoxide, titanium tetra-tert-butoxide and, preferably, titanium tetraisopropoxide (hereinafter also simply referred to as titanium isopropoxide). The use of these titanium alkoxides as raw materials gives rise to the formation of low-boiling alcohols as reaction by-products, which can be easily removed from the reaction environment by evaporation, washing with water or distillation.

The preferred 1,3-diols of formula [1] for achieving the new method are 1,3-butanediol, 3-methyl-1,3-butanediol, 2,2-dimethyl-1,3-butanediol, 2,2,4-trimethyl-1,3-pentanediol, 1,3-propanediol, 2,2-dimethyl-1,3-propanediol, 2,2-diethyl-1,3-propanediol, 2-methyl-2-propyl-1,3-propanediol, 2-butyl-2-ethyl-1,3-propanediol, 2-methyl-1,3-propanediol, 2,2-dibutyl-1,3-propanediol, 2,2-isobutyl-1,3-propanediol, 2-ethyl-2-methyl-1,3-propanediol, 2-sec-butyl-2-methyl-1,3-propanediol, 2-ethyl-1,3-hexanediol, 2-butyl-1,3-octanediol and 1,3-nonanediol. The use of 2-ethyl-1,3-hexanediol is particularly preferred.

The compound of Ti(IV) is mixed with the 1,3-diol of formula [1] in a Ti:diol molar ratio between 1:0.85 and 1:1.20, i.e. between 15% molar deficiency and 20% molar excess of diol with respect to the moles of titanium. Said ratio is preferably between 1:0.95 and 1:1.05. According to the preferred embodiment of the new method, the titanium alkoxide is reacted with the 1,3-diol of formula [1] in a Ti:diol molar ratio 1:1.015, i.e. with an excess equal to 1.5% moles of 1,3-diol with respect to the moles of titanium.

The mixing of the reactants can be carried out under various pressure and temperature conditions. Since the reaction between the compound of Ti(IV) and the 1,3-diol is exothermic, during this step of the process, the temperature of the reaction mixture increases in the absence of external temperature adjustment. Preferably, the reaction temperature is maintained between 50 and 75° C., more preferably between 60° C. and 70° C., by means of a thermostatic bath. The reactants can be mixed together in any order; to improve control of the exothermic reaction, however, it is preferable to mix the 1,3-diol with the reaction solvent and subsequently add the compound of titanium under stirring and in subsequent portions.

The process is conducted in an organic solvent (or a mixture of organic solvents) immiscible with water and inert with respect to the reagents, products and by-products that develop in the course of the reaction. The solvent is preferably selected from the compounds with boiling point greater than 70° C., belonging to the following classes: saturated or unsaturated, cyclic or acyclic, linear or branched, possibly halogenated aliphatic hydrocarbons, aromatic hydrocarbons, ethers, glycol ethers and mixtures thereof. Suitable solvents for the purposes of the invention are for example: cyclohexane, n-heptane, n-octane, various fractions of petroleum distillates (petroleum ethers, turpentine, naphthas), o-xylene, m-xylene, p-xylene, decalin, diethylene glycol dibutyl ether, 3,3'-methylenebis(oxymethylene)bis-heptane and mixtures thereof. Preferably, the solvent in which this step is carried out is the same solvent subsequently used for the preparation of the digital printing ink; this way, there is no need to purify the titanium derivative from the solvent following the preparation thereof.

The solvent used in step (i) is further preferably characterized by at least one of the following physicochemical properties:
  viscosity≤5 cP, more preferably ≤3 cP, at 20° C.;
  initial boiling point≥135° C.;
  flash point≥100° C. in a sealed vessel;
  surface tension at 20° C. between 25 and 35 mN/m.

According to a particularly preferred embodiment, the solvent used is a mixture of linear and/or branched, cyclic and/or acyclic aliphatic hydrocarbons (naphtha), with an initial boiling point greater than 160° C. and even more preferably greater than 230° C. and a flash point greater than 100° C. Solvents or mixtures of solvents with a high flash point are preferred as their use allows the risk factors present in performing the process to be reduced.

After the reaction between the starting compound of titanium and the 1,3-diol, step (i) provides for removal of the reaction by-products, which can take place by evaporation, by extraction with water and subsequent separation of the immiscible aqueous and organic phases, or by distillation. In the case in which a titanium alkoxide has been used in step (i), on completion of the exotherm due to mixing of the reactants, the reaction mixture is heated to a temperature 5-10° C. higher than the boiling temperature of the alcohol that forms as a reaction by-product of said alkoxide and the 1,3-diol. For example, in the case in which titanium isopropoxide is used, the reaction mixture is heated to a temperature of at least 87-90° C., since the isopropyl alcohol that forms as a by-product has a boiling temperature of about 82° C. at atmospheric pressure. The by-product (alcohol) is removed from the reaction environment by distillation, on completion of which, before moving on to the next step, the reaction mixture is cooled to a temperature of <100° C., preferably ≤85° C.

Step (i) generally has a duration of between 30 and 300 minutes. In the case in which an inorganic compound of titanium is used in this step, the reaction by-products include, among others, inorganic acids; since even a few ppm of inorganic acid residue in the ink can cause corrosion problems to the digital printing heads, the use of these inorganic compounds of Ti(IV) entails a lengthening of step (i) of the process for the complete removal of the reaction by-products; he organic compounds of Ti(IV) are thus preferred as starting reagents of the process of the invention.

In step (ii) of the process of the invention, water in a molar ratio of $H_2O$:Ti≥2, preferably ≥3, more preferably in a molar ratio between 3:1 and 5:1, is added under stirring to the reaction mixture resulting from step (i). The water for use in the process has preferably a conductivity of less than 9.0 µS/cm. The addition of water can take place in a single portion or, preferably, through subsequent partial additions to keep the course of the exothermic reaction that takes place in this step under better control. A white-coloured, stirrable suspension is formed after adding the water. Removal of the unreacted water and of the by-products of the reaction mixture can take place by sedimentation and separation of the immiscible aqueous and organic phases or by distillation. In the case in which an organic compound of titanium and in particular an alkoxide are used in step (i), the removal of water takes place by distillation: on completion of the addition of water, the reaction mixture is heated to a temperature 5-10° C. higher than the boiling temperature of the alcohol that forms as a reaction by-product from the titanium alkoxide, distilling the reaction by-products and the unreacted water. According to the preferred embodiment of the method, step (ii) has a duration of between 3 and 8 hours. On completion of step (ii), which is easily identifiable since discontinuation of the distillation is observed, the reaction mixture typically presents as a viscous, amber yellow colour liquid.

In the case in which an inorganic or organo-inorganic compound of titanium is used in step (i), the unreacted water and the reaction by-products that are soluble in the aqueous phase are removed from the reaction environment at ambient temperature, by sedimentation and separation of the two mutually immiscible phases.

On completion of the removal of the unreacted water and the by-products, the reaction mixture resulting from step (ii) is subjected to the maturation (aging) step (iii). During this step, the reaction mixture is brought to a temperature between 170 and 200° C., preferably 180-190° C., and maintained at this temperature for 16-50 hours, preferably for 32-36 hours. During the maturing step (iii) reactions take place that lead to the formation of water, which is distilled together with any reaction by-products. It has been observed that if the temperature of the maturing step (iii) is brought to above 200° C. there is a deterioration of the hydrolytic stability of the titanium derivative obtainable by the method.

Steps (i) to (iii) can be independently carried out both in air and in an inert environment; the entire process is preferably carried out under a stream of nitrogen, with a flow rate of the latter of 3-15 l/min. Distillation operations are thus accelerated and the safety level of the entire process is increased. In case the maturing step is carried out under a stream of nitrogen, the weight of the amount of distilled water can be less than the weight of the amount distilled under the same implementing conditions but in the absence of a stream of nitrogen, due to entrainment of a part of the distillate by the inert gas.

Steps (i) to (iii) of the process can be independently conducted both at atmospheric pressure (approximately 1013 mbar), and under vacuum, generally at a pressure of about 250 mbar.

On completion of maturing step (iii) a clear yellow solution is obtained from which, upon drying, it can be obtained the organic titanium derivative object of the second aspect of the present invention, in the form of a pulverulent yellow solid with a Ti (metal) content between 20.0 and 27.0% by weight with respect to the dry material; using the compound of Ti(IV) and the 1,3-diol in the preferred ratios in step (i), said Ti content is between 22.0 and 25.0%.

In a preferred embodiment, the preparation process of the new titanium derivative is conducted in the presence of a solvent that can be used for the preparation of the ink according to the invention. According to this preferred embodiment, the clear yellow solution obtained on completion of step (iii) can be directly used in the preparation of the digital printing ink according to the invention, described hereunder, without isolating the titanium derivative contained therein.

The mixture obtainable from this preferred embodiment of the process comprises:
(a) 18.0-21.0% by weight of Ti with respect to the solution, in the form of Ti-diol obtainable from the method described above;
(b) at least an organic solvent immiscible with water selected from the group consisting of saturated or unsaturated, cyclic or acyclic, linear or branched, possibly halogenated aliphatic hydrocarbons, aromatic hydrocarbons, ethers, glycol ethers and mixtures thereof.

The titanium derivative obtainable from the above-described process presents as a titanium-containing organo-inorganic polymer characterized in that the polymeric fraction having Log M≥3 has an at least bimodal molecular weight distribution and represents at least 70% by weight of the derivative itself. The molecular weight distribution is herein defined "at least" bimodal since, in all measurements performed by the inventors on samples of the invention, two main peaks are always clearly distinguishable, while in some cases at least one of these seems to be formed by the convolution of two or more peaks that are very close to each other, which could be resolved in a more evident manner by implementing different measurement conditions. In these cases, the curve that represents the molecular weight distribution in logarithmic form also has, in addition to an absolute minimum that divides the two main peaks, one or more relative minimums. A situation of this type is for example illustrated in the molecular weight distribution graph reported in FIG. 1, wherein the first peak roughly comprised between 3.4<Log M<3.8 is formed by two peaks that largely overlap each other.

The titanium derivatives of the invention are surprisingly stable to hydrolysis, i.e. they give positive results in the hydrolytic stability test described below and are compatible with the organic derivatives of chromium soluble in organic solvents used in the preparation of ceramic digital printing inks. In the description that follows, the concentration of the metal compounds is expressed as a percentage by weight of the metal with respect to the total weight of the ink, unless otherwise indicated.

Said new titanium derivatives can therefore be usefully employed in the preparation of a ceramic digital printing ink, object of the third aspect of the invention, comprising the following components:
(A) 6.0-12.0%, preferably 6.5-11.0% by weight, of Ti in the form of the titanium derivative of the invention;
(B) 0.5-2.0%, preferably 0.8-1.2% by weight of Cr in the form of an organic compound of Cr(III) and/or 1.0-3.0% by weight of Ni in the form of an organic compound of Ni;
(C) at least an organic solvent selected from saturated or unsaturated, cyclic or acyclic, linear or branched, possibly halogenated aliphatic hydrocarbons, aromatic hydrocarbons, ethers, glycol ethers, esters, carbonates and mixtures thereof.

The ink according to the invention comprises as component (A) the titanium derivative according to the invention as described above and as component (B) an organic compound of Cr(III) and/or an organic compound of Ni, said organic compounds preferably being selected from salts and/or complexes of Cr(III) and/or Ni with linear or branched, aliphatic or aromatic C5-C18 monocarboxylic acids and mixtures thereof. Particularly preferred for the preparation of the ink of the invention are chromium neodecanoate, chromium 2-ethylhexanoate and mixtures thereof and/or nickel 2-ethyl hexanoate, nickel neodecanoate and mixtures thereof. Said chromium and/or nickel derivatives are available on the market or can be easily obtained by reacting a low-molecular weight chromium and/or nickel derivative (chromium acetate or nickel acetate for example) and a corresponding C5-C18 monocarboxylic acid, in the presence of a suitable solvent. Preferably, in the ink of the invention, the Ti to Cr weight ratio is between 13:1 and 5:1, more preferably between 10:1 and 7:1.

The component (C) of the ink according to the invention is an organic solvent or a mixture of organic solvents selected from saturated or unsaturated, cyclic or acyclic, linear or branched, possibly halogenated aliphatic hydrocarbons, aromatic hydrocarbons, ethers, glycol ethers, esters and carbonates. Component (C) is selected from n-octane, linear, branched and/or cyclic C10-C20 petroleum distillates, turpentine, petroleum ether, o-xylene, m-xylene, p-xylene, diethylene glycol dibutyl ether, tripropylene glycol monobutyl ether, diethylene glycol monobutyl ether, triethylene glycol monobutyl ether, dibutylcarbonate, isopropyl myristate, dioctyl adipate, 3,3'-methylenebis(oxymethylene)bis-heptane, diethyleneglycol n-butyl ether acetate, saturated C16-C18 and unsaturated C18 fatty acid methyl esters and mixtures thereof. These solvents are commonly available on the market.

The component (C) of the ink according to the invention also preferably has at least one of the following physico-chemical properties:
it is immiscible with water;
viscosity≤5 cP, more preferably ≤3 cP, at 20° C.;
initial boiling point≥135° C.;
flash point >100° C. (sealed vessel);
surface tension at 20° C. between 25 and 35 mN/m.

According to a particularly preferred variant, component (C) consists of a mixture of linear, branched and/or cyclic C15-C20 hydrocarbons, with an initial boiling point greater than 160° C., even more preferably greater than 230° C., and a flash point greater than 100° C.

According to one variant of the invention, the ink further comprises a fourth component (D), consisting of Sb in the form of triphenylantimony, in an amount such that the amount of the metal represents between 6.0 and 9.0% by weight, preferably 7.8-8.5% of the ink.

The presence of component (D) in the ink according to the invention causes a variation in the colour tone produced as a result of firing of the decorated material, which shifts towards an orange yellow shade.

The ink according to the invention preferably possesses one or more of the following physicochemical properties:
- viscosity measured at the printer ejection temperature according to the below-described method between 8.0 and 20.0 mPa·s, preferably between 9.0 and 18.0 mPa·s, more preferably between 11.0 and 16.0 mPa·s;
- surface tension at 20° C. of between 25 and 35 mN/m.

The viscosity of the ink measured at the printer ejection temperature within the above-indicated range is a particularly relevant parameter so as to be able to use the ink according to the invention in the digital printers that are currently on the market.

The ink of the invention can also contain up to a maximum of 10% by weight of the starting 1,3-diol, which cannot be easily separated from the reaction product. Higher amounts must in any case be removed as it has been observed that amounts greater than 10% by weight of 1,3-diol in the ink of the invention cause an unacceptable increase in the viscosity of the ink itself. In case of presence of 1,3-diol, the above-reported percentages for components (A) and (B) are maintained in the ink of the invention, thus decreasing the amount of solvent (C).

In the fourth and final aspect thereof, the invention relates to a decoration method of ceramic materials by means of digital printing comprising the use of the above-described ink.

Said method preferably comprises the following operational steps:
(a) preparing a ceramic material mixed with an additive, said material comprising titanium dioxide ($TiO_2$) and/or antimony trioxide ($Sb_2O_3$);
(b) applying the ink of the invention by means of digital printing onto the ceramic material resulting from step (a);
(c) baking the ceramic material resulting from step (b) at a temperature of between 900° C. and 1300° C.

Step (a) of the method provides the preparation of a ceramic material mixed with an additive, said ceramic material comprising the following components:
(1) titanium dioxide in an amount preferably between 0.05 and 0.70% by weight, more preferably between 0.10 and 0.30% and/or antimony trioxide in an amount between 0.10 and 2.00%, preferably between 0.20 and 1.00%; and
(2) a mixture of ceramic raw materials in an amount preferably between 98.00 and 99.95%.

The above-indicated percentages relate to the weight of the dry ceramic material.

The titanium dioxide used as component (1) in the decoration method can be indifferently in the form of rutile, anatase or mixtures thereof. The ceramic raw materials in their natural state normally contain $TiO_2$, generally in an amount less than 0.5% by weight. The above-reported percentages of component (1) relate to the amount of titanium dioxide intentionally added to the ceramic slurry and that is in excess with respect to the $TiO_2$ naturally present in the ceramic raw materials used. According to a preferred variant of the invention, the ceramic material mixed with an additive comprises titanium dioxide in combination with antimony trioxide.

Component (2) consists of a mixture of ceramic raw materials, such as for example clay, kaolin, feldspar, sand, etc., the composition of which varies depending on the type of ceramic material that is to be produced.

Step (a) can be accomplished by following different operating modes.

According to a first possibility, titanium dioxide and/or antimony trioxide are mixed with the ceramic raw materials before forming of the ceramic material, simultaneously or sequentially in any order. According to this first variant, titanium dioxide and antimony trioxide can be added in the correct proportions to the entire quantity of ceramic raw materials constituting the material to be decorated, according to the so-called "full body" mode. Alternatively, a ceramic material mixed with an additive, comprising components (1) and (2) in the above-reported percentages, can be applied onto the surface of the ceramic material to be decorated by means of the "double loading" technique.

Titanium dioxide and/or antimony trioxide can be mixed with the ceramic raw materials upstream of the full processing cycle, i.e. with the dry ceramic raw materials before grinding; alternatively, the additives (component (1)) can be suspended in water and added to the aqueous suspension of ceramic raw materials (2) (slip) discharged from the grinding mill. The "full body" and "double loading" operating modes are generally used for the production of products that must be polished after firing, up to a depth of even 3 mm, to obtain coloured surfaces with mirror effect.

Alternatively and preferably, step (a) is conducted by applying an aqueous suspension comprising between 50.0 and 70.0% by weight of ceramic material mixed with an additive having the above-reported composition and between 30.0 and 50.0% by weight of water, onto the surface of the pre-formed raw ceramic material to be decorated (green). Application of the aqueous suspension onto the ceramic material to be decorated can take place by spraying, typically in airless cabins, or by deposition of a uniform layer of suspension, using for instance the Vela® system of Eurotecnica—Ceramic Engineering Division (Sassuolo, Mo.) or bell application. Said suspension is applied in an amount between 200 and 1000 $g/m^2$, preferably between 400 and 900 $g/m^2$. This variant of the method is useful for producing ceramic objects, which, after firing, are not subjected to subsequent processing of the surface or to the production of materials that are polished after firing, i.e. ceramic materials which surface is abraded with grinding wheels, removing a surface thickness of between 10 and 200 μm. When the method is carried out according to this variant, an engobe consisting of an aqueous suspension of ceramic raw materials is optionally applied between the raw ceramic material and the layer of ceramic material mixed with an additive. The layer of engobe, several microns thick, has the function of improving adhesion of the ceramic material mixed with an additive to the support and, in some cases, of making the surface to be coloured whiter.

Before the subsequent decorating step (b), the ceramic material thus obtained can be dried at temperatures below 100° C. to remove excess water present in the formed material, and subsequently cooled. However, during the decorating step, the ceramic material mixed with an additive generally has a temperature that can reach 70° C.

In step (b), the ceramic material mixed with an additive resulting from step (a) is decorated by means of digital printing, preferably ink-jet printing. The inventors have observed that optimal performances are obtained with the ink of the invention when the temperature of the ceramic material mixed with an additive subjected to decoration is ≤50° C., preferably ≤35° C. During this step the ink of the invention can be applied onto the ceramic material mixed with an additive in varying amounts, depending on the type of decoration to be produced and on the capacity of the ceramic material to absorb the ink. The amount applied is generally between 2 and 80 g/m$^2$ of coloured surface, preferably between 5 and 60 g/m$^2$, even more preferably between 10 and 40 g/m$^2$.

An organic compound selected from saturated or unsaturated, cyclic or acyclic, linear or branched, possibly halogenated aliphatic hydrocarbons, aromatic hydrocarbons, ethers, glycol ethers, esters, linear or branched C5-C18 monocarboxylic acids and mixtures thereof, can be applied onto the decorated surface of the ceramic material mixed with an additive by means of digital printing, engraved-roller screen printing or spraying, between the decorating and firing steps. Said compound is preferably selected from linear, branched and/or cyclic C10-C20 petroleum distillates, diethylene glycol, propylene glycol, polypropylene glycol, diethylene glycol dibutyl ether, tripropylene glycol methyl ether, dipropylene glycol methyl ether, tripropylene glycol monobutyl ether, triethylene glycol monobutyl ether, saturated and unsaturated C18-C24 carboxylic acid methyl esters, neodecanoic acid, 2-ethylhexanoic acid and mixtures thereof. A mixture that comprises at least one of the above-indicated organic compounds and one or more technical additives of various kinds, such as surfactants, dispersing agents, defoamers, etc., can also be used to carry out this step. Preferably, said organic compounds or blend are applied in an amount of between 10 and 300 g per m$^2$ of treated surface; increasing this amount increases the penetration depth of the ink inside the ceramic material. The above-reported amounts allow a penetration depth of between 100 and 2000 μm to be obtained.

The decorated ceramic material is subsequently fired in step (c) at a temperature of between 900 and 1300° C. The firing cycle, i.e. the firing temperature and time, depends on the type of ceramic material that is to be produced. Normally, the firing cycle of the ceramic material mixed with an additive can vary slightly with respect to the firing cycle of the same material not mixed with an additive, particularly as regards the maximum firing temperature. The maximum firing temperature is generally in a range of ±20° C. with respect to the maximum firing temperature used for the same ceramic material not mixed with an additive (standard firing cycle). Based on his knowledge of the art, a person skilled in the art is able to make the necessary changes to the standard firing cycle of a specific ceramic material to make it suitable for firing of the ceramic material mixed with an additive.

Since in order to obtain the different shades of colour by means of digital printing, a mixture of colours that constitute the set of printing inks is needed, according to a preferred variant of the method, step (b) is implemented by applying an ink set comprising the ink according to the above-described invention onto the ceramic material to be decorated. Inks known in the field, such as the inks described in patent EP 1272574, which are useful for obtaining the colour cyan, magenta and black, or the solvent-based inks described in patent application WO 2009/077579, can be usefully employed as inks that are part of the set.

According to a particularly preferred variant, the decorating method comprises the following operational steps:
(a1) preparing a ceramic material mixed with an additive comprising titanium dioxide and/or antimony trioxide and amorphous silica;
(b1) applying, by means of ink-jet digital printing onto the ceramic material resulting from step (a1), an ink set comprising:
the ink of the invention (I1);
an ink (I2) comprising an organic solvent and at least an organic compound of cobalt;
an ink (I3) comprising an organic solvent and at least an organic compound of iron;
(c) firing the ceramic material resulting from step (b1) at a temperature of between 900° C. and 1300° C.

Step (a1) of the method comprises preparing a ceramic material, mixed with an additive, preferably comprising the following components:
(1) $TiO_2$ in an amount between 0.05 and 0.70% by weight, preferably between 0.10 and 0.30% and/or $Sb_2O_3$ in an amount between 0.10 and 2.00%, preferably between 0.20 and 1.00%;
(2) a mixture of ceramic raw materials in an amount between 88.00 and 99.45% by weight; and
(3) amorphous silica in an amount between 0.50 and 10.00% by weight, more preferably between 2.00 and 7.00%.

The above-indicated percentages relate to the weight of the dry ceramic material. The amorphous silica used as component (3) is selected from precipitated silica, silica gel and mixtures thereof and is characterised by active surface area $S \geq 100$ m$^2$/g, wherein said active surface area is defined by the formula $S = A \times Gr$, in which Gr is the granulometric fraction between 5 and 60 μm for precipitated silica and between 1 and 60 microns for silica gel, and A is the surface area of the silica in m$^2$/g measured by means of the B.E.T. method. The particle size of silica is the one obtained using a granulometer with laser diffraction detector as provided by the ISO 13320-1 (1999) standard, provided with wet sampler. The silica samples are normally treated before analysis (for instance by stirring, treatment with ultrasounds or the addition of surfactants) so as to obtain a stable dispersion of the particles in the solvent used for the test (usually water). These treatments break the labile tertiary structures (aggregates) and the measured particle size corresponds to that of the stable secondary particles stable (agglomerates). Further characteristics of the amorphous silica suitable for carrying out the method are described in detail in patent application WO 2005/063650 A2. If the amorphous silica is mixed with components (1) and (2) prior to grinding, said amorphous silica can have an initial particle size greater than 60 μm and an active surface area of less than 100 m$^2$/g. When the amorphous silica is added to components (1) and (2) downstream of the grinding process, said amorphous silica preferably has an initial particle size of between 5 and 60 μm for the precipitated silica and of between 1 and 60 μm for the silica gel.

According to a particularly preferred variant of the invention, the ceramic material mixed with an additive comprises titanium dioxide in combination with antimony trioxide and amorphous silica.

Step (b1) is accomplished by applying by means of a digital printer, preferably an ink-jet printer, an ink set comprising, in addition to the ink according to the invention described above, an ink (I2) comprising an organic solvent and at least an organic compound of cobalt, and an ink (I3) comprising an organic solvent and at least an organic compound of iron. According to a further variant of the method, the ink set useful for carrying out step (b1) further comprises a fourth ink (I4) comprising an organic solvent and at least an organic compound of cobalt in combination with at least an organic compound of iron. The organic compounds useful for the preparation of inks (I2) to (I4) are preferably selected from salts and/or metal complexes of the above-indicated chromophore metals with linear or branched aliphatic or aromatic C5-C18 monocarboxylic acids and mixtures thereof. Particularly preferred for the preparation of the inks (I2) and (I4) are cobalt 2-ethyl hexanoate, cobalt neodecanoate, cobalt laurate, cobalt stearate, cobalt benzoate, cobalt oleate, cobalt iso-nonanoate and mixtures thereof. Particularly preferred for the preparation of inks (I3) and (I4) are iron 2-ethyl hexanoate, iron neodecanoate, iron laurate, iron stearate, iron iso-nonanoate, iron benzoate and mixtures thereof. Said inks preferably contain:

(I2) Co in an amount between 4.0 and 9.5% by weight, preferably between 7.5 and 9.0%;
(I3) Fe in an amount between 1.5 and 7.5% by weight, preferably between 6.0 and 7.0%;
(I4) Fe in an amount between 2.0 and 7.0% by weight and Co in an amount between 1.0 and 5.0% by weight; preferably Fe in an amount between 3.0 and 5.0% by weight and Co in an amount between 1.5 and 4.0% by weight.

In addition, inks (I2), (I3) and (I4) can contain small traces of organic salts and/or complexes of other chromophore metals to modify their L*a*b* coordinates.

Solvents useful for the preparation of inks (I2) to (I4) are preferably selected from: aromatic hydrocarbons, aliphatic hydrocarbons, ethers, esters, ketones, glycols, halogenated hydrocarbons and mixtures thereof. Suitable aromatic hydrocarbons are for example toluene, xylenes, terpenes and aromatic petroleum distillates. Of the aliphatic hydrocarbons, saturated, cyclic or acyclic aliphatic hydrocarbons such as octane and various fractions of petroleum distillates (e.g. naphthas, etc.) are preferable. Of the ethers usable as solvents, dibutyl ether, dialcoxyethanes and alkoxy ethanols (e.g. 2-methoxyethanol), diethylene glycol dibutyl ether, tripropylene glycol methyl ether, dipropylene glycol methyl ether, tripropylene glycol monobutyl ether, diethylene glycol monoethyl ether, triethylene glycol monobutyl ether can for example be cited. Of the esters useful as solvents there are, for example, n-butyl acetate and ethyl lactate. Of the ketones usable as solvents, methyl isobutyl ketone and cyclohexanone can for example be cited. Of the glycols useable as solvents in the above-described inks, glycerol, ethylene glycol, diethylene glycol, propylene glycol are preferred. The preparation of organic compounds useful for the preparation of inks (I2) and (I4), as well as the preparation of the inks themselves, is described in patent application WO 2009/077579 A1.

Some non-limiting examples of the embodiment of the present invention are reported below.

EXAMPLES

The physicochemical properties are determined according to the following methods.

Molecular weights: absolute molecular weights, molecular weight distribution and statistical averages (Mn, Mw) are measured using the GPC (Gel Permeation Chromatography) technique by means of a chromatograph equipped with a Knauer K501 isocratic pump and three detectors: a diffused light detector, a Viscotek TD270 differential viscometer and a Knauer Mod. 2300 refractive index detector. Absolute molecular weights and molecular weight distribution are determined by means of the diffused light detector (measurements at 90° and 7° with respect to the incident ray). The chromatographic peak area is determined using the refractive index detector. The stationary phase consists of two mixed-bed columns connected in series: a first Resipor PL (Polymer Laboratory Ltd) Mixed D column (length 300 mm, diameter 7.8 mm, average particle size 5 µm) and a second Tosoh TSK Gel (Mixed E) G2550H column (length 300 mm, diameter 7.8 mm, average particle size 5 µm). The columns are thermostated at 35° C. HPLC grade THF with a 1 ml/min flow is used as mobile step. The acquisition and processing of the analytical data provided by the three detectors are managed by the Omnisec 4.6 (Viscotek) software, assuming as concentration value the value reported in the tables that summarise the results of the examples and do/dc=0.0704 ml/g. The Recovery value reported in the tables below represents the weight fraction of the injected sample for which the molecular weight distribution has been determined. Only the fraction of sample with 5≥Log M≥3 is considered for determination of the Recovery.

As part of the measures directed to obtain the molecular weight parameters, it is also obtained the value of Intrinsic Viscosity (IV) of the tested specimens, as the direct result of the measure of the Viscotek TD270 differential viscometer.

Ti content: for this determination, one capsule of porcelain is brought to constant weight by oven-drying at 50° C. Approximately 3.0 g of sample are precisely weighed in the porcelain capsule. The capsule is placed in a ventilated oven for 24 hours at 180° C. and then heated in a muffle furnace under the following conditions: constant heating speed of 5° C./min, maximum temperature of 1000° C., residence time at maximum temperature 5 min. The muffle furnace is then cooled to 200° C. in about 8 hours. On completion of the heating cycle, the capsule is placed in the dryer in which cooling to ambient temperature is completed. The capsule is weighed and the weight of the residue (R) is determined by subtracting the tare weight. The weight of the Ti in the residue is obtained by multiplying the weight of the residue (R) by 0.5993 (weight fraction of Ti in the $TiO_2$, which is obtained from calcination in the muffle furnace). The percentage of Ti in the samples is determined by dividing the weight of the Ti in the residue by the initial weight of the sample and multiplying by 100.

1,3-diol content in the ink: the analysis is performed by IR spectrophotometry with a Thermo Nicolet Avatar 330 instrument in ATR mode (crystal ZnSe), with a resolution of 0.48 $cm^{-1}$, averaging 80 spectra and with a movement velocity of the interferometer mirror of 0.42 cm/sec. The normalisation and baseline subtraction process is performed on each spectrum before any further processing of the data, using EZ OMNIC 6.2 data collection software. The amount of 1,3-diol in the ink is determined by measuring the height (net absorbance) of the peak at 3350 $cm^{-1}$, using the following calibration curve:

$$y=0.0119x+0.0107(R^2=0.989)$$

wherein:
y=net absorbance; and
x=% in weight of diol

Viscosity: viscosity is measured using a CS10 Bohlin (Malvern) rheometer in the titanium cylinder/stainless steel cup-and-bob C25 DIN 53019 configuration; PSL calibration standard Rheotek PSL oil with viscosity at 40° C.=14.23 cP.

Before performing a measurement, instrument calibration is checked using a standard with known viscosity, at the reference temperature of the standard. The correction factor "f" to be applied to the analytical viscosity datum is determined according to the following equation:

$$f = \text{visc. TS}/\text{visc. MS}$$

in which "visc. TS"=viscosity of the standard and "visc. MS"=analysed sample viscosity.

The end of stroke of the instrument is placed at 0.150 mm; 20 ml of solution to be analysed are then loaded into the rheometer, while removing the excess. The sample to be analysed is thermostated at the temperature at which the measurement is to be performed (+/−0.1° C.). When the thermal equilibrium is reached, a pre-shearing at 300 1/s of 30 s duration is performed followed by a resting period of 10 s. The measurement is performed by acquiring the viscosity data with a shearing of 50 1/s, during 300 s, with the acquisition of 1 datum/s. The measurement is repeated 2 times. For each sample, the average viscosity value of the last 6 data of the second measurement, multiplied by the correction factor "f", is adopted as viscosity value.

Surface Tension: the surface tension of the samples is measured by means of a Sinterface BPA-1 S model bubble pressure tensiometer equipped with a stainless steel Sinterface capillary having the following characteristics: radius=0.130 mm; calibration coefficient=0.794; reference bubble volume=6.40; reference dead time=48 ms; immersion depth=5 mm. After performing the self-calibration procedure of the instrument, the surface tension of the reference solvent (Tripropylene glycol n-butyl ether, TPnB, CAS: 55934-93-5-supplier Sigma Aldrich Cod. 484229; surface tension 29.7 mN/m at 25° C.) is measured. The reference solvent is placed in a beaker thermostated at 25° C. into which the capillary is immersed. The viscosity value (expressed in cSt) and density value (expressed in g/cm$^3$) relating to the sample to be analysed are entered in the instrument. Surface tension measurement is performed in the lifetime interval between 0.01 and 30 s, for a measurement time of 30 min. The surface tension value of the reference solvent 1 s (1 Hz), $TS_{refTPnB@25C}$ is noted.

The surface tension of the sample to be analysed is subsequently measured and the datum at 1 s (1 Hz) of the sample, $TS_{sample\ not\ correct}$ is noted. The surface tension value of the sample is determined by the relation:

$$TS_{sample} = \frac{S_{sample\ not\ correct}}{S_{refTPnB@25C}} \times 29.7$$

Density: the density measurement is performed using a portable DMA 35N Anton Paar densitometer, thermostating the sample at 25° C. Each sample is analysed three times, adopting the average of the three values as the result.

Mass spectrometry: Applied Biosystem 4800 Plus MALDI-TOF/TOF spectrometer. An Nd:YAG laser with λ=335 nm pulsed at 200 Hz was used for desorption of the sample. Operating mode: Reflectron. Method of acquisition: positive ions. Spectral window acquired: 300-4000 m/z. Each spectrum is averaged over 2000 acquisitions. The spectra are obtained on solid samples, using dithranol as matrix. Dithranol dispersed in cyclohexane is deposited on the sample holder plate; after evaporation of the solvent, the sample dissolved in cyclohexane is deposited on the matrix.

Conductivity: conductivity is measured with a WTW InoLab Cond 720 conductivity meter with LR325/01 electrode (cell constant 0.1 cm$^{-1}$), using a calibration solution with 0.9 μS/cm at 20° C. (Hamilton) conductivity as calibration standard for the instrument. In order to perform the measurement, the sample is thermostated at 20±0.2° C.

Hydrolysis stability: for this evaluation, 6 g of ink are vigorously mixed in a glass test tube with 1 g of demineralised water. The mixture is filtered under vacuum with a Millipore filter apparatus equipped with 5-micron filters to remove any solid impurities. Subsequently, the mixture is left in the hermetically sealed test tube for 30 days at a temperature of 50° C. The test is deemed successful (YES) if at the end of the contact period the ink presents as a clear/transparent solution free of suspended solids or sediments. The test is deemed unsuccessful (NO) if at the end of the observations period suspended solids or sediments are observed in the ink.

Compatibility: 200 g of ink are stirred using a mechanical stirrer at 100 rpm for 30 minutes at a temperature of 20° C. The homogeneous solution thus obtained is allowed to stand for a maximum of 7 days, during which time it is checked daily. The test is deemed successful (YES) if at the end of the resting period the ink presents as a clear/transparent solution free of suspended solids or sediments. The test is deemed unsuccessful (NO) if at the end of the observation period, or on occasion of interim checks, the presence of suspended solids or sediments is observed in the ink.

Example 1

Into a glass reactor, at ambient temperature and pressure, were loaded 25.04 kg of 2-ethyl-1,3-hexanediol and 10.8 kg of the solvent Siosol WS AZ 99 (Siochem), an aliphatic naphtha with boiling range 232-280° C. and viscosity 3.3 cP at 20° C. Inside the reactor there was an inert atmosphere consisting of nitrogen. 47.97 kg of titanium isopropoxide were added to the mixture slowly and under stirring. On completion of the addition, the reaction mixture was heated to 96° C. and maintained at this temperature until complete distillation of the isopropanol formed as a by-product (distillate weight 19.7 kg). The reaction mixture was then cooled to 45° C. 10.0 kg of demineralised water (conductivity of 5.0 μS/cm) were subsequently added. The temperature of the reactor was brought to 90° C., distilling the reaction by-products and water. The distillation was conducted under a stream of nitrogen, with a flow rate of 2 l/min. On completion of the distillation, the temperature of the reactor was brought to 182° C., progressively increasing the nitrogen flow rate to 10 l/min (maturation): the mixture was maintained at this temperature for 32 hours. On completion of the maturing step, the mixture was slowly cooled to 50° C. and unloaded from the reactor. A sample of the mixture containing the titanium derivative was dried, thus obtaining a yellow solid with a Ti content of 22.5% by weight.

FIG. 1 reports the GPC molecular weight distribution curve of the titanium derivative obtained in the example, recorded under the above-reported conditions. For the GPC analysis, a sample of the mixture obtained on completion of the procedure was dried in an oven at 160-170° C. at a pressure of 12-15 mmHg (1,600-2,000 Pa) and subsequently dissolved in THF at ambient temperature under gentle stirring. The characteristic molecular weight distribution parameters are reported in Table 1:

TABLE 1

| Measured characteristic | Measurement unit | First peak | Second peak |
|---|---|---|---|
| Mn | Dalton | 2.197 | 10.100 |
| Mw | Dalton | 3.259 | 11.065 |
| Mw/Mn | / | 1.483 | 1.096 |
| IV | dl/g | 0.0070 | 0.0066 |
| Weight fraction | / | 0.613 | 0.387 |
| Recovery | % | 93.972 | |
| Sample conc. | mg/ml | 13.25 | |

The titanium derivative obtained according to the above-described method shows a bimodal molecular weight distribution and a Recovery of about 94%, i.e. a fraction of product having Log M≥3 equal to about 98%.

Example 2

The preparation process of the titanium derivative described in Example 1 was repeated, reducing the time of the maturing step from 32 to 16 hours. On completion of this step, the reaction mixture was slowly cooled to 50° C. and unloaded from the reactor. The viscous yellow mixture containing the titanium derivative of the invention had a Ti content of 18.22% by weight with respect to the total weight of the mixture.

Figure 2:
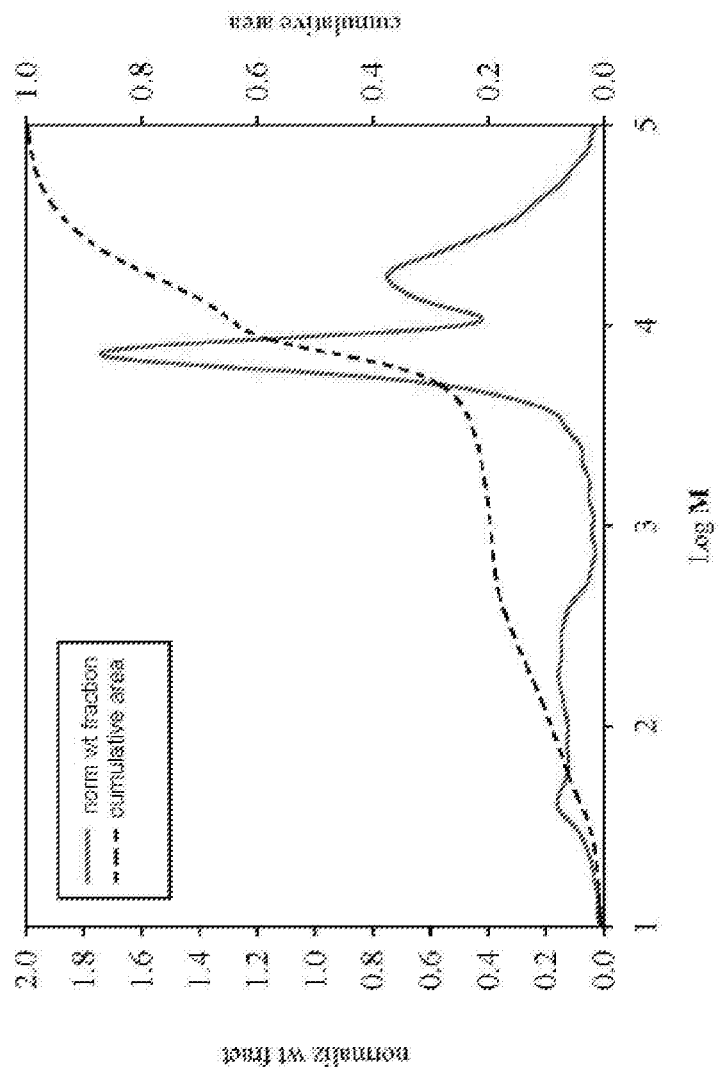

FIG. 2 reports the GPC molecular weight distribution curve of the titanium derivative obtained by the method of the invention, recorded under the above-reported conditions. For the GPC analysis, a sample of the mixture obtained on completion of the procedure was dried in an oven at 160-170° C. at a pressure of 12-15 mmHg (1,600-2,000 Pa) and subsequently dissolved in THF at ambient temperature under gentle stirring. The characteristic molecular weight distribution parameters are reported in Table 2:

TABLE 2

| Measured characteristic | Measurement unit | First peak | Second peak |
|---|---|---|---|
| Mn | Dalton | 2.391 | 7.293 |
| Mw | Dalton | 2.687 | 9.386 |
| Mw/Mn | / | 1.124 | 1.287 |
| IV | dl/g | 0.0067 | 0.0047 |
| Weight fraction | / | 0.561 | 0.439 |
| Recovery | % | 71.563 | |
| Sample conc. | mg/ml | 26.90 | |

The titanium derivative obtained according to the procedure of this example shows a bimodal molecular weight distribution and a product fraction having Log M≥3 equal to about 80%.

Example 3

479.7 g of titanium isopropoxide were added slowly and under stirring to a mixture containing 250.4 g of 2-ethyl-1,3-hexanediol and 108 g of Siosol WS AZ 99 (Siochem) solvent in a four-neck flask equipped with a distillation head provided with rectification column (Vigreux). The exothermic reaction was maintained at a temperature of about 65° C. by means of a thermostated bath. On completion of the exotherm, the reaction mixture was heated to 90° C., distilling isopropanol. After about 4 hours distillation of the by-product was complete (weight of the first distillate=192.0 g). The reaction mixture was then cooled to 50° C. At this temperature, 100 g of demineralised water (conductivity 5.0 μS/cm) were added, slowly and under stirring. The reaction mixture was brought to 90° C. distilling the reaction by-products (mainly isopropanol) and the unreacted water. On completion of the distillation (weight of the second distillate=270.8 g), the mixture was brought to 180° C. and maintained at this temperature for 24 hours, for the maturing step. During this last step a total of a further 8.3 g of water and by-products were distilled. The entire process was carried out at ambient pressure, inertizing the reaction environment with nitrogen. On eliminating the solvent, a yellow solid was obtained, having a Ti (metal) content of 24.3% by weight with respect to dry weight.

Figure 3:
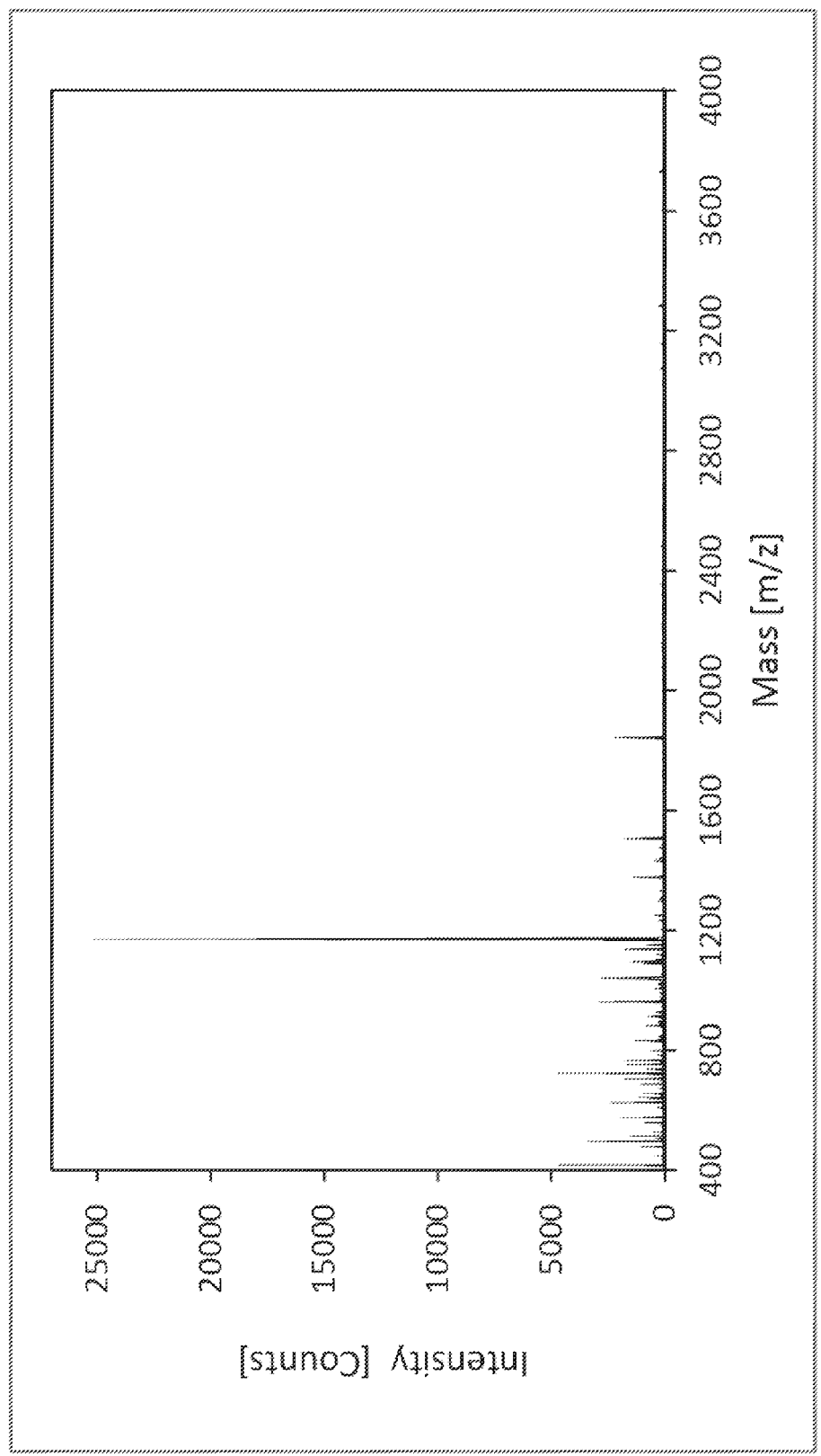
FIG. 3 reports the mass spectrum of a titanium derivative of the invention.

FIG. 3 reports the mass spectrum of the titanium derivative obtained. The spectrum shows a base peak at m/z=1169.98. The most intense peak present in the mass spectrum of a compound is defined as "base peak"; normally the base peak is attributed an arbitrary height equal to 100 and all the other peaks present in the spectrum are normalised with respect thereto.

The base peak is the most intense peak of the spectrum as it represents the ion that is most likely to form during the ionisation that takes place in the mass spectrometer. It is generally considered a characteristic fingerprint of the compound to which it relates.

Example 4

544.45 g of titanium isopropoxide were added, slowly and under stirring, to a mixture containing 284.2 g of 2-ethyl-1,3-hexanediol and 114.4 g of cis/trans-decalin mixture (Reagent grade—Sigma Aldrich) in a four-neck flask equipped with a distillation head provided with rectification column (Vigreux). The exothermic reaction was maintained at a temperature of about 65° C. by means of a thermostated bath. On completion of the exotherm, the reaction mixture was heated to 90° C., distilling isopropanol. After about 5 hours the distillation of the by-product was complete. The reaction mixture was then cooled to 40° C.

At this temperature, 112.5 g of demineralised water (conductivity 5.0 μS/cm) were added, slowly and under stirring. The reaction mixture (milky white) was brought to 90° C. distilling the reaction by-products (mainly isopropanol) and water.

On completion of the distillation, the mixture was brought to 180° C. and maintained at this temperature for 36 hours, for the maturing step. The entire process was carried out at ambient pressure, inertizing the reaction environment with nitrogen.

Having removed the solvent by drying with a rotary evaporator (160° C.; vacuum at 2 mbar up to constant weight of the residue), a pale yellow solid was obtained having a Ti (metal) content of 23.2% by weight with respect to the dry product.

Figure 4:
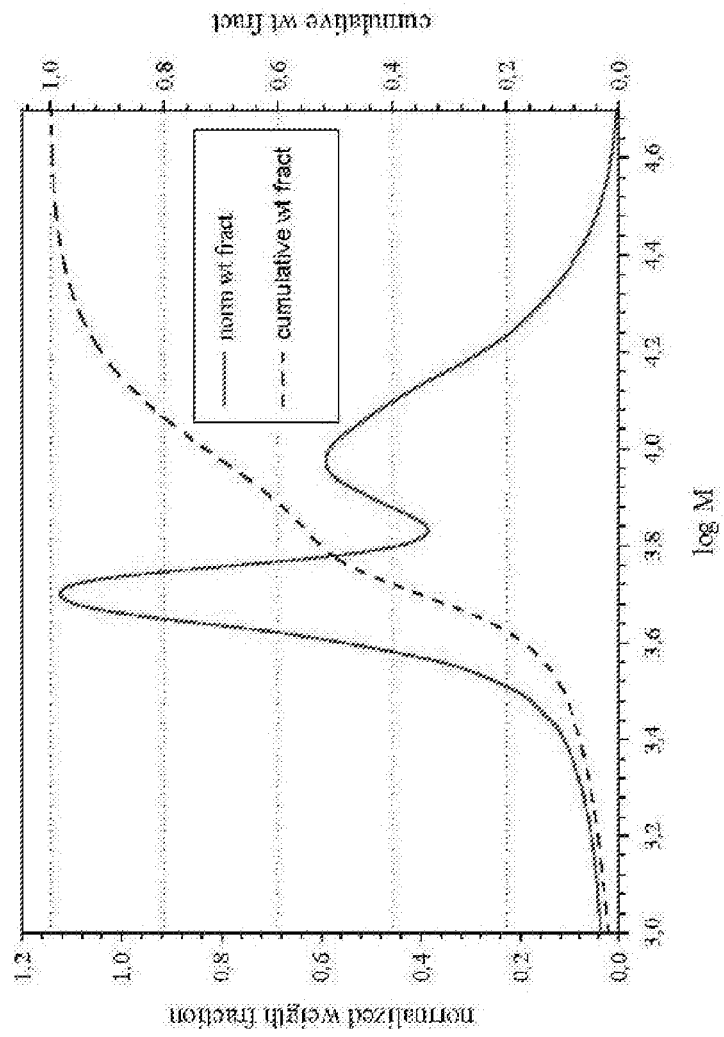

FIG. 4 reports the GPC molecular weight distribution curve of the titanium derivative obtained in the example, recorded under the above-reported conditions. For the GPC analysis, a solid sample of the product was dissolved in THF at ambient temperature, under gentle stirring.

The characteristic molecular weight distribution parameters are reported in Table 3:

TABLE 3

| Measured characteristic | Measurement unit | First peak | Second peak |
|---|---|---|---|
| Mn | Dalton | 2.970 | 10.693 |
| Mw | Dalton | 3.415 | 11.970 |
| Mw/Mn | / | 1.15 | 1.119 |
| IV | dl/g | 0.0068 | 0.0067 |
| Weight fraction | / | 0.561 | 0.439 |

TABLE 3-continued

| Measured characteristic | Measurement unit | First peak | Second peak |
|---|---|---|---|
| Recovery | % | | 93.163 |
| Sample conc. | mg/ml | | 13.4 |

The titanium derivative obtained according to the procedure of this example shows a bimodal molecular weight distribution and a fraction of product having Log M≥3 equal to about 97%.

Example 5 (Comparison)

The preparation process of glycol titanates described in Example 1 of U.S. Pat. No. 2,643,262 was repeated. 150.74 g of 2-ethyl-1,3-hexanediol at (Aldrich, 97%) and 284.22 g of titanium isopropoxide, were mixed in a laboratory flask at ambient temperature and pressure, in the presence of 130 g of heptane as a solvent. The reaction mixture was placed under stirring for about 2 hours. 130 g of demineralised water were then added and the mixture was left under stirring for about 30 min.

Once stirring was complete, the mixture was allowed to rest to allow complete separation of the two immiscible phases present. The organic phase containing the glycol titanate was separated from the aqueous phase and the solvent was evaporated in a rotary evaporator at atmospheric pressure and temperature of 50° C. 56.0 g of white powder having a titanium content of 23.99% by weight, with respect to the dry weight, was obtained.

Figure 5:
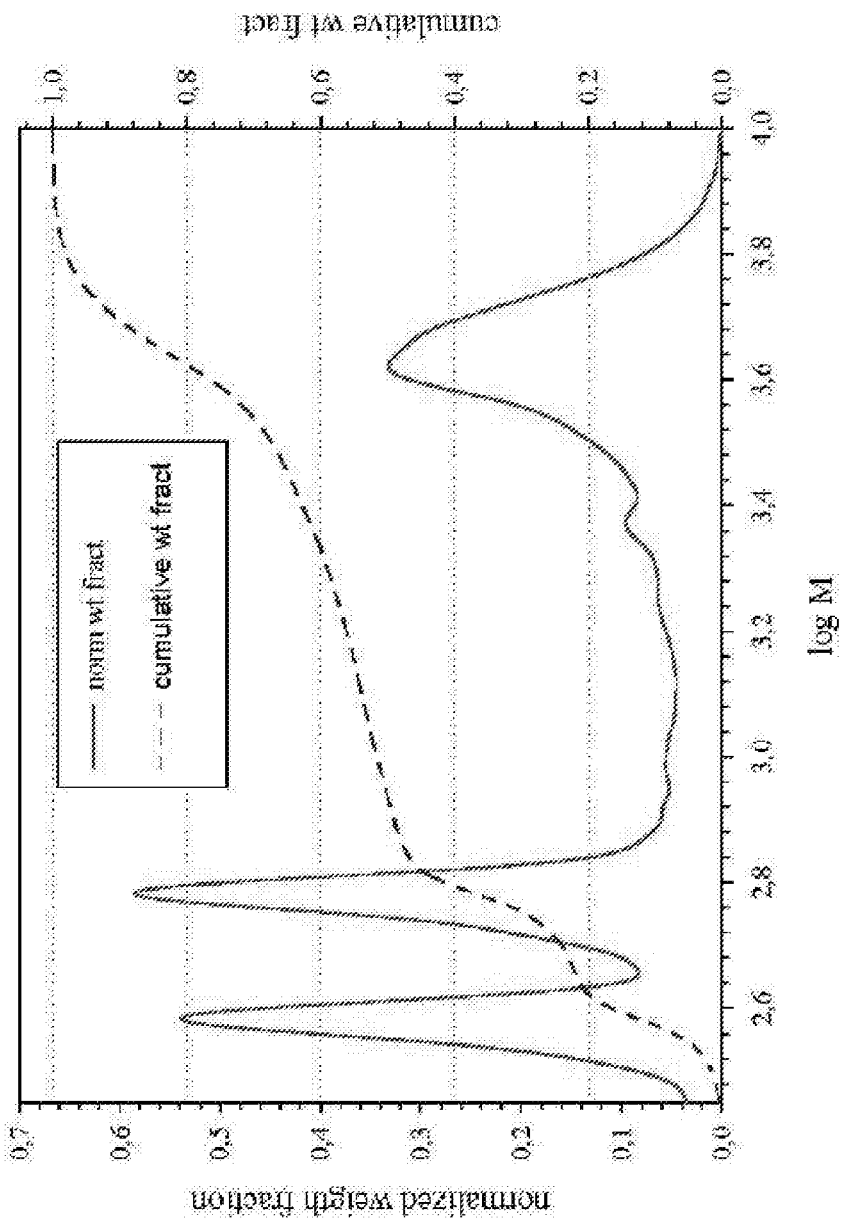
FIG. 5 reports the molecular weight distribution curve of a titanium derivative of the prior art.

FIG. 5 reports the GPC molecular weight distribution curve of the glycol titanate. For the GPC analysis, a sample of the mixture obtained on completion of the procedure was dried in an oven at 160-170° C. at a pressure of 12-15 mmHg and subsequently dissolved in THF at ambient temperature under gentle stirring.

The characteristic parameters of the molecular weight distribution curve are reported in Table 4:

TABLE 4

| Measured characteristic | Measurement unit | Peak |
|---|---|---|
| Mn | Dalton | 479 |
| Mw | Dalton | 5,282 |
| Mw/Mn | | 11.025 |
| IV | dl/g | 1.00 |
| Recovery | % | 38.04 |
| Sample conc. | mg/ml | 15.43 |

The fraction of glycol titanate with values of Log M≥3 represents about 52% of the product. In addition, the molecular weight distribution of said fraction is monomodal.

Table 5 reports the viscosities, at a temperature of 45° C., measured according to the above-reported method, of 12% by weight solutions of Ti (with respect to the weight of the solution) of the samples of the new titanium derivative obtained in Examples 1-4 and of the glycol titanate of comparative Example 5. In order to perform the measurement, about 500 g of solution are prepared in a 1000 ml beaker, solubilising with Siosol WS AZ 99 (Siochem) the amount of sample required to obtain a final solution with a 12.0% by weight concentration of Ti. The solution to be analysed is stirred at 200 rpm with a magnetic stirrer until complete homogenisation before performing the measurement.

TABLE 5

| Example | Viscosity (mPa · s) at 45° C. |
|---|---|
| 1 | 18.2 |
| 2 | 19.5 |
| 3 | 14.9 |
| 4 | 16.5 |
| 5 (Comparison) | 29.3 |

As is noted from the data in Table 5, with the same solvent and concentration of Ti, using the titanium derivatives obtained according to the new method, solutions with a significantly lower viscosity are obtained with respect to the solutions obtainable using the glycol titanates of comparative Example 5. This means that by using the new titanium derivatives according to the invention it is possible to obtain inks having a high concentration of Ti, with viscosity falling within the range required for use with the digital printers currently on the market. Said inks will therefore be able to develop a very saturated yellow colour after firing of the ceramic material.

Examples 6 to 8 and Comparative Examples 9 and 10

The new titanium derivatives obtained in Examples 1, 2 and 4 and the glycol titanate of comparative Example 5 were used for the preparation, respectively, of the inks of Examples 6 to 8 and of comparative Examples 9 and 10, having the compositions reported in Table 6 (the comparative examples are marked with an asterisk). The same table reports the compositions of the inks, the results of the ink hydrolytic stability and component compatibility tests carried out according to the above-reported methods.

The inks were prepared by mixing, at ambient temperature and under stirring, the mixtures "as reactor" containing the titanium derivatives obtained in Examples 1, 2 and 4 and the glycol titanate of comparative Example 5 with: (B) Chromium neodecanoate (Cr-NEODEC) obtained by reaction between chromium acetate and neodecanoic acid in molar ratio Cr:acid=1:3.3 or Chromium 2-ethylhexanoate (Cr-EES) obtained by reaction between chromium acetate and 2-ethylhexanoic acid in molar ratio Cr:acid=1:3.4; and (C) Tecnol GT (Oleotecnica), an aliphatic naphtha with boiling range 270-320° C., flash point 136° C. and viscosity 4.1 mPa·s at 30° C. and Siosol WS AZ99 or diethylene glycol dibutyl ether (BDG—Clariant).

The components (E) and (F) are impurities due to the raw materials used for the preparation of components (A) and (B).

TABLE 6

| Ex. | Components Type | % (w/w) | Metal (%, w/w) | Viscosity at 45° C. (mPa · s) | Hydrolytic stability | Compatibility |
|---|---|---|---|---|---|---|
| 6 | (A) Ti derivative Ex. 1 | 30.1 | 6.80 | 13.6 | YES | YES |
| | (B) Cr-NEODEC | 9.2 | 0.85 | | | |

TABLE 6-continued

| Ex. | Components Type | % (w/w) | Metal (%, w/w) | Viscosity at 45° C. (mPa · s) | Hydrolytic stability | Compati- bility |
|---|---|---|---|---|---|---|
|  | (C) 89% Tecnol GT, 11% Siosol WS AZ99 | 59.5 | / |  |  |  |
|  | (E) 2-ethyl-1,3-hexanediol | 0.4 | / |  |  |  |
|  | (F) Neodecanoic acid | 0.8 | / |  |  |  |
| 7 | (A) Ti derivative Ex. 2 | 30.1 | 6.80 | 14.0 | YES | YES |
|  | (B) Cr-NEODEC | 9.2 | 0.85 |  |  |  |
|  | (C) 88% Tecnol GT, 12% Siosol WS AZ99 | 59.1 | / |  |  |  |
|  | (E) 2-ethyl-1,3-hexanediol | 0.8 | / |  |  |  |
|  | (F) neodecanoic acid | 0.8 | / |  |  |  |
| 8 | (A) Ti derivative Ex. 4 | 40.5 | 9.40 | 11.0 | YES | YES |
|  | (B) Cr-EES | 9.2 | 1.00 |  |  |  |
|  | (C) BDG | 48.5 | / |  |  |  |
|  | (E) 2-ethyl-1,3-hexanediol | 0.8 | / |  |  |  |
|  | (F) 2-ethylhexanoic acid | 1.0 | / |  |  |  |
| 9* | (A) Ti derivative Ex. 5 | 28.3 | 6.80 | 17.6 | / | NO (2 days) |
|  | (B) Cr-NEODEC | 9.2 | 0.85 |  |  |  |
|  | (C) 88.6% Tecnol GT, 11.4% Siosol WS AZ99 | 61.7 | / |  |  |  |
|  | (F) neodecanoic acid | 0.8 | / |  |  |  |
| 10* | (A) Ti derivative Ex. 5 | 33.1 | 7.95 | 11.2 | NO - suspended solids | YES |
|  | (B) Cr-EES | 9.2 | 1.00 |  |  |  |
|  | (C) BDG | 56.7 | / |  |  |  |
|  | (F) 2-ethylhexanoic acid | 1.0 | / |  |  |  |

Example 11

The Ti derivative obtained in Example 1 was used for the preparation of ink 11, having the composition and the physicochemical characteristics reported in Table 7. The ink was prepared by mixing, at ambient temperature and under stirring, the mixture "as reactor" containing the titanium derivative obtained in Example 1, with:

(B) Chromium neodecanoate (Cr-NEODEC) obtained as described in the preceding examples;

(C) solvent consisting of 88.7% Tecnol GT (Oleotecnica) and 11.3% Siosol WS AZ 99 (Siochem).

The components (E) and (F) are impurities due to the raw materials used for the preparation of components (A) and (B).

TABLE 7

| Composition ink 11 | | |
|---|---|---|
| Type | (% w/w) | Metal (%, w/w) |
| (A) Ti derivative Ex. 1 | 30.1 | 6.80 |
| (B) Cr-NEODEC | 10.9 | 1.00 |
| (C) solvent | 57.7 | / |
| (E) 2-ethyl-1,3-hexanediol | 0.4 | / |
| (F) Neodecanoic acid | 1.0 | / |
| Physicochemical properties | | |
| Density (25° C.) | 0.942 g/cm³ | |
| Viscosity (45° C.) | 15.1 mPa · s | |
| Surface tension (25° C.) | 30.0 mN/m | |

The ink was applied, by means of an ink jet printer, onto a ceramic support obtained by pressing a ceramic slurry for porcelain stoneware (Meta Neutro White 9100), onto which had been deposited, by means of the Vela® System, 750-800 g/m² of a suspension containing 31% water and 69% ceramic material mixed with an additive having the following composition:

(1) 0.1% $TiO_2$ in the form of rutile;
(2) 94.4% mixture of ceramic raw materials having the following composition:
  44.5% soda feldspar SY (Gimat SrI);
  22.2% white clay LY1 N (Whitam SrI);
  12.1% kaolin CC31 (Sibelco Italia SpA);
  8.5% nepheline Altaflux 45 (Gimat SrI);
  8.5% feldspar Flos 7 (Minerali Industriali SrI);
  2.1% litomet PE60 (Whitam SrI);
  2.1% talc Luzenac EC60 (Gimat SrI);
(3) 0.5% $Sb_2O_3$;
(4) 5.0% silica gel with $d_{50}$=11 μm, S=260.6 m²/g (Gr=91.86%; A=283.7 m²/g).

To facilitate grinding, 0.45% of Fluicer PD73 (Ceramco SpA) and 0.5% Rhodiaceram P 10% aqueous solution (Ceramco SpA) were added to the ceramic material mixed with an additive.

Before application of the layer of ceramic material mixed with an additive, approximately 400 g/m² of an engobe consisting of a suspension containing 67.5% of a mixture of ceramic raw materials having the below-reported mineralogical composition and 32.5% of water were applied onto the ceramic support by airless spraying:

22.0% F245/TC frit (Smalticeram Unicer SpA);
18.0% zirconium silicate KE standard (Gimat SrI);
11.0% clay PD Hywite Superb (Imerys Ceramics);
10.0% ground kaolin KCR (Eurosabbie SrI);
10.0% feldspar FS900/L (Gimat SrI);
9.0% soda feldspar SY (Gimat SrI);
9.0% nepheline Altaflux 45 (Gimat SrI);
7.0% Flos 8 sand (Tecnominerali SrI);
4.0% Litomet PE60 (Whitam SrI);

To facilitate grinding, 0.1% of Fluicer PD73 (Ceramco SpA) was added to the engobe.

The ink of the invention was applied onto the ceramic support in an amount equal to 16.0 g/m² by means of a Kerajet Plotter (encoder) P140 printer, equipped with SEIKO GS12 printing heads; print resolution 1015×360 dpi;

BIN 2 (30 picoliters); print temperature 58° C.; head RANK: A=29.0–B=29.0; PZT Volt head; 20.9/20.9.

The decorated ceramic material was fired in a roller kiln with a standard porcelain stoneware firing cycle ($T_{max}$=1215° C. for 60 minutes).

Table 8 reports the Lab values measured with two different colorimeters: the first set of data was obtained using a Dr. Lange Spectrapen Model colorimeter (LZM224—Standard No. 1009); the second set of data was obtained using an i1 Pro spectrophotometer marketed by X-RITE Inc. Measurements were performed both on the "natural" material, i.e. on the surface of the material not subjected to further treatments after the firing step, and on the lapped material, i.e. on the surface of the material after removal of a surface layer with a thickness of between 0.05-1.00 mm. The "base" data were obtained from the measurements performed on a portion of ceramic support mixed with an additive not coloured with the ink of the invention.

TABLE 8

|     |         |      | L     | a     | b     |
|-----|---------|------|-------|-------|-------|
| (1) | natural | base | 84.19 | −0.02 | 6.79  |
|     |         | ink  | 78.33 | 0.59  | 32.39 |
|     | polished| base | 85.47 | −0.08 | 6.78  |
|     |         | ink  | 79.38 | 0.16  | 30.95 |
| (2) | natural | base | 84.06 | −0.42 | 5.87  |
|     |         | ink  | 79.38 | 0.15  | 32.98 |
|     | polished| base | 84.45 | −0.42 | 6.05  |
|     |         | ink  | 80.71 | −0.33 | 31.26 |

Example 12

Two inks, 12 and 13, were prepared with a solvent (component (C)) at least partially miscible with water, as detailed below.

Inks 12 and 13 were prepared by mixing, at ambient temperature and under stirring, the mixture "as reactor" containing the titanium derivative obtained in Example 4, with:
(B) Chromium 2-ethylhexanoate (Cr-EES) as described in Examples 6 to 8; and:
(C) as solvents, were used either Diethylene glycol dibutyl ether (butyl diglyme), or Tripropylene glycol n-butyl ether TPnB, Sigma Aldrich.

The components (E) and (F) are impurities due to the raw materials used for the preparation of components (A) and (B).

The two inks have the composition and the viscosity reported in Table 9.

TABLE 9

| Ink | Components Type        | (%, w/w) | Metal (%, w/w) | Viscosity at 45° C. (mPa · s) |
|-----|------------------------|----------|----------------|-------------------------------|
| 12  | (A) Ti derivative Ex. 4| 40.5     | 9.40           | 12.4                          |
|     | (B) Cr-EES             | 9.2      | 1.00           |                               |
|     | (C) Butyl diglyme      | 48.5     | /              |                               |
|     | (E) 2-ethyl-1,3-hexanediol | 0.8  | /              |                               |
|     | (F) 2-ethylhexanoic acid | 1.0    | /              |                               |
| 13  | (A) Ti derivative Ex. 4| 27.6     | 6.4            | 13.0                          |
|     | (B) Cr-EES             | 7.4      | 0.8            |                               |
|     | (C) TPnB               | 63.6     | /              |                               |
|     | (E) 2-ethyl-1,3-hexanediol | 0.6  | /              |                               |
|     | (F) 2-ethylhexanoic acid | 0.8    | /              |                               |

Example 13

The ink of Example 7 (Table 6) and inks 12 and 13 were used in tests of decoration of ceramic materials. The tests were carried out on a ceramic support mixed with an additive (composition detailed below) coloured with different amounts of inks, on the same ceramic material with additive coloured with inks and subsequently treated with a blend of organic compounds to enhance penetration of the ink inside the ceramic material, and, for comparison purposes, on the same ceramic material with additive not coloured with an ink.

The inks (and optionally penetration enhancer) were applied, by means of an ink jet printer, onto a ceramic support obtained by pressing a ceramic slurry for porcelain stoneware (Meta Ultrawhite), onto which had been deposited, by means of the Vela® System, 750-800 g/m² of a suspension in water, having density about 1.72 g/l, of a ceramic material mixed with an additive having the following composition:

(1) 0.1% $TiO_2$ in the form of rutile;
(2) 94.4% mixture of ceramic raw materials, having the following composition:
   44.9% soda feldspar SY (Gimat SrI);
   19.1% nepheline Spectrum 45 Bitossi (Altaflux 45);
   11.6% kaolin Puraflo CC31 (Sibelco Italia SpA);
   10.6% ground kaolin KCR (KDG);
   8.5% feldspar Flos 7 (Minerali Industriali SrI);
   3.2% corundum EKR 220 (Gimat SrI);
   2.1% litomet PE60 (Whitam SrI);
(3) 0.5% $Sb_2O_3$;
(4) 5.0% silica gel with $d_{10}$=4.7 μm, $d_{50}$=7.5 μm, $d_{90}$=13.1 μm (data measured as described in the text), B.E.T. surface area=409.4 m²/g.

To facilitate grinding, 0.12% of Fluicer PD73 (Ceramco SpA) was added to the ceramic material mixed with an additive.

In different tests, the inks were applied in two different amounts, 15 and 30 g/m². The penetration enhancer had viscosity equal to 14.5 mPa·s at 45° C. and the composition (by weight):
Tecnol GT 19.1%;
2-ethylhexanoic acid 0.5%;
TPnB 36.1%;
PPG2000 44.3%.

PPG2000 is polypropylene glycol, CAS No. 25322-69-4, marketed by Gamma Chimica of Lainate, Italy, having cinematic viscosity of 440 mm²/s at 23° C. The penetration enhancer was applied in an amount of 50 g/m², in five application cycles of 10 g/m² each, after the application of the ink; in the table that follows, the indication P.E. means that the penetration enhancer was used, in the said amount.

The ink jet printer used was model Kerajet Plotter (encoder) P140, equipped with SEIKO GS12 printing heads; print resolution 1015×360 dpi; BIN 2 (30 picoliters); print temperature 48-58° C.; head RANK: A=29.0–B=29.0; PZT Volt head; 20.9/20.9.

The specimens (decorated or not) were fired in a roller kiln with a standard porcelain stoneware firing cycle ($T_{max}$=1215° C. for 55 minutes). Colorimetric measurements were performed on not coloured specimens ("Base" data), on coloured specimens not subjected to further treatments after the firing step (indicated in the table below as "NAT"), and on lapped specimens, i.e., on the surface of fired specimens after removal of a surface layer with a thickness of 0.01 ("LAP 1" in the table) or 0.065 mm ("LAP 2" in the table).

Table 11 reports the L*a*b* values measured with an i1 Pro spectrophotometer marketed by X-RITE Inc.

TABLE 11

| Treatment | Ink | | | | | | | | |
|---|---|---|---|---|---|---|---|---|---|
| | Ex. 7, Table 6 | | | Ink 12 | | | Ink 13 | | |
| | L* | a* | b* | L* | a* | b* | L* | a* | b* |
| NAT - Base | 85.21 | 0.21 | 7.38 | 85.52 | 0.38 | 7.49 | 85.29 | 0.22 | 7.35 |
| NAT - 15 g/m² ink | 80.32 | 0.1 | 35.14 | 75.23 | 7.45 | 52.14 | 79.49 | 1.22 | 40.73 |
| NAT - 30 g/m² ink | 76.69 | 3.9 | 48.57 | 70.35 | 13.77 | 50.56 | 75.79 | 5.69 | 50.83 |
| LAP 1 - Base | 85.36 | 0.23 | 7.59 | 85.56 | 0.39 | 7.59 | 84.91 | 0.23 | 7.43 |
| LAP 1 - 15 g/m² ink + P.E. | 82.56 | 0.08 | 16.03 | 80.49 | 0.75 | 20.32 | 81.78 | 0.24 | 17.74 |
| LAP 1 - 30 g/m² ink + P.E. | 80.88 | 0.61 | 20.22 | 78.09 | 2.38 | 28.57 | 80.92 | 0.57 | 18.66 |
| LAP 2 - Base | 86.16 | 0.37 | 7.62 | 86.15 | 0.43 | 7.59 | 85.88 | 0.33 | 7.56 |
| LAP 2 - 15 g/m² ink + P.E. | 83.68 | 0.13 | 13.94 | 81.01 | 0.96 | 20.25 | 83.46 | 0.10 | 16.60 |
| LAP 2 - 30 g/m² ink + P.E. | 81.88 | 0.57 | 19.31 | 79.20 | 2.44 | 31.52 | 82.27 | 0.52 | 19.12 |

Comments to the Results

As highlighted by the data reported in the tables, the organic titanium derivatives of the invention allow the preparation of a digital printing ink characterized by the combination of a high concentration of titanium, an unexpected compatibility of the various components of the ink itself, an excellent stability to hydrolysis and an optimum combination of physicochemical characteristics, in particular viscosity and surface tension, necessary for the use of said inks in the ceramic digital printings devices present on the market. This combination of factors not only makes the ink of the invention extremely versatile and usable with a wide range of ink-jet printers currently on the market, but also makes it able to develop a saturated yellow colour after firing, which is very useful for producing a wide gamut of colours when inserted in a digital printing ink set. In addition, the high stability to hydrolysis of this ink makes it easy to use, overcoming problems relating to clogging of the printing heads and the related downtimes due to deterioration of the titanium-based inks currently on the market.

Although various embodiments of the present invention have been described and shown, the invention is not restricted thereto, but may also be embodied in other ways within the scope of the subject-matter defined in the following claims.

What is claimed is:

1. A process for the preparation of an organic titanium derivative, comprising the following steps:
   (i) mixing an organic and/or inorganic compound of titanium (IV) and a 1,3-diol of formula [1]:

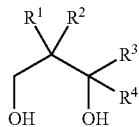

[1]

wherein $R^1$, $R^2$, $R^3$ and $R^4$ are independently selected from H and a linear or branched C1-C6 alkyl radical, in a Ti:diol molar ratio of between 1:0.85 and 1:1.20, in the presence of at least an organic solvent immiscible with water and subsequent removal of reaction by-products;
   (ii) adding water to the reaction mixture in a $H_2O$:Ti≥2 molar ratio and subsequent removal of unreacted water and reaction by-products;
   (iii) maturing the reaction mixture at a temperature of 180-200° C. for 16-50 hours.

2. The process according to claim 1, wherein the organic and/or inorganic compound of titanium (IV) used in step (i) is selected from titanium halides, titanium sulphate, titanium hydroxide, chloro-isopropyl-titanate, titanium oxotitanates or titanium alkoxides of formula $Ti(OR)_4$, wherein R is a linear or branched C1-C4 alkyl radical.

3. The process according to claim 1, wherein the 1,3-diol used in step (i) is 2-ethyl-1,3-hexanediol.

4. The process according to claim 1, wherein the organic solvent used in step (i) is selected from saturated or unsaturated, cyclic or acyclic, linear or branched, possibly halogenated aliphatic hydrocarbons; aromatic hydrocarbons; ethers; glycol ethers and mixtures thereof.

5. A titanium derivative obtainable by the process according to claim 1, in the form of a titanium-containing organo-inorganic polymer characterized in that the polymeric fraction having Log M≥3 has an at least bimodal molecular weight distribution and represents at least 70% by weight of the derivative.

6. An ink containing a titanium derivative of claim 5, comprising:
   (A) 6.0-12.0% by weight of Ti in the form of said titanium derivative;
   (B) 0.5-2.0% by weight of Cr in the form of an organic compound of Cr(III) and/or 1.0-3.0% by weight of Ni in the form of an organic compound of Ni;
   (C) at least a organic solvent selected from saturated or unsaturated, cyclic or acyclic, linear or branched, possibly alogenated aliphatic hydrocarbons, aromatic hydrocarbons, ethers, glycol ethers, esters, carbonates, and mixtures thereof.

7. The ink according to claim 6, further comprising as fourth component, (D), triphenylantimony, $Sb(C_6H_5)_3$, in an amount such that the metal represents between 6.0 and 9.0% by weight of the ink.

8. The ink according to claim 6, wherein the weight ratio of Ti to Cr is between 13:1 and 5:1.

9. The ink according to claim 6, further comprising up to 10% by weight of the starting 1,3-diol.

10. A ceramic printing method that uses the ink of any claim 6, comprising the following operational steps:

(a) preparing a ceramic material mixed with an additive comprising titanium dioxide ($TiO_2$) and/or antimony trioxide ($Sb_2O_3$);
(b) applying said ink by means of digital printing on the ceramic material resulting from step (a);
(c) firing the ceramic material resulting from step (b) at a temperature of between 900° C. and 1300° C.

11. An ink set comprising:
the ink according to claim 6;
a second ink (I2) comprising an organic solvent and at least an organic compound of cobalt; and
a third ink (I3) comprising an organic solvent and at least an organic compound of iron.

12. The ink set according to claim 11, further comprising a fourth ink (I4) comprising an organic solvent and at least an organic compound of cobalt in combination with at least an organic compound of iron.

* * * * *